United States Patent
Kawahara

(10) Patent No.: US 11,846,808 B2
(45) Date of Patent: Dec. 19, 2023

(54) OPTICAL TRANSDUCER FOR ENDOSCOPE, ENDOSCOPE, AND MANUFACTURING METHOD FOR OPTICAL TRANSDUCER FOR ENDOSCOPE

(71) Applicant: OLYMPUS CORPORATION, Tokyo (JP)

(72) Inventor: Kosuke Kawahara, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 398 days.

(21) Appl. No.: 17/387,274

(22) Filed: Jul. 28, 2021

(65) Prior Publication Data
US 2021/0356730 A1 Nov. 18, 2021

Related U.S. Application Data

(63) Continuation of application No. PCT/JP2019/015526, filed on Apr. 9, 2019.

(51) Int. Cl.
*G02B 6/30* (2006.01)
*A61B 1/00* (2006.01)
(Continued)

(52) U.S. Cl.
CPC ............ *G02B 6/30* (2013.01); *A61B 1/0011* (2013.01); *A61B 1/00013* (2013.01);
(Continued)

(58) Field of Classification Search
CPC ............ G02B 23/2423; G02B 23/2469; G02B 23/2476; G02B 23/2484; G02B 23/26;
(Continued)

(56) References Cited

U.S. PATENT DOCUMENTS 10,905,311 B2 * 2/2021 Nakagawa ............. A61B 1/051
11,366,304 B2 * 6/2022 Nakagawa ........... G02B 6/4243

FOREIGN PATENT DOCUMENTS

JP   H07-333467 A   12/1995
JP   2004-317632 A   11/2004
(Continued)

OTHER PUBLICATIONS

International Search Report dated Jul. 16, 2019 received in PCT/JP2019/015526.

*Primary Examiner* — Michael P Mooney
(74) *Attorney, Agent, or Firm* — Scully, Scott, Murphy & Presser, P.C.

(57) ABSTRACT

An optical transducer for endoscope includes an optical element, an optical fiber, and a fiber holding member including a first holding member including a first principal surface and a second principal surface and a second holding member in which a third principal surface is disposed to face the second principal surface, a first through-hole into which the optical fiber is inserted, being formed in the first holding member, the optical element being mounted on a fourth principal surface. A trench connected to the first through-hole and including openings respectively on opposed two side surfaces is formed on the second principal surface. Only a part of a distal end portion of the optical fiber is observable from the openings of the trench.

11 Claims, 11 Drawing Sheets

(51) Int. Cl.
    *G02B 6/42*         (2006.01)
    *G02B 23/24*      (2006.01)
    *G02B 23/26*      (2006.01)

(52) U.S. Cl.
    CPC ......... *G02B 6/424* (2013.01); *G02B 23/2484* (2013.01); *A61B 1/00165* (2013.01); *G02B 23/26* (2013.01)

(58) Field of Classification Search
    CPC .......... G02B 23/30; G02B 6/30; G02B 6/424; G02B 6/4202; G02B 6/4242; A61B 1/0011; A61B 1/00114; A61B 1/00117; A61B 1/00124; A61B 1/00135; A61B 1/00165; A61B 1/018; A61B 1/042; A61B 1/05; A61B 1/00013; A61B 18/149
    See application file for complete search history.

(56) References Cited

FOREIGN PATENT DOCUMENTS

| | | |
|---|---|---|
| WO | 2018/037551 A1 | 3/2018 |
| WO | 2018/134933 A1 | 7/2018 |
| WO | 2019/038929 A1 | 2/2019 |

\* cited by examiner

OPTICAL TRANSDUCER FOR ENDOSCOPE, ENDOSCOPE, AND MANUFACTURING METHOD FOR OPTICAL TRANSDUCER FOR ENDOSCOPE

CROSS REFERENCE TO RELATED APPLICATION

This application is a continuation application of PCT/JP2019/015526 filed on Apr. 9, 2019, the entire contents of which are incorporated herein by this reference.

BACKGROUND OF THE INVENTION

1. Field of the Invention

The present invention relates to an optical transducer for endoscope including a fiber holding member in which a first through-hole is formed, an optical fiber being inserted into the first through-hole and fixed by transparent resin, an endoscope including an optical transducer for endoscope including a fiber holding member in which a first through-hole is formed, an optical fiber being inserted into the first through-hole and fixed by transparent resin, and a manufacturing method for an optical transducer for endoscope including a fiber holding member in which a first through-hole is formed, an optical fiber being inserted into the first through-hole and fixed by transparent resin.

2. Description of the Related Art

An endoscope includes an image pickup device at a distal end portion of an elongated insertion section. In recent years, an image pickup device with a large number of pixels has been examined in order to display a high-quality image. When the image pickup device with a large number of pixels is used, an image signal amount transmitted from the image pickup device to a signal processing apparatus (a processor) increases. Therefore, in electric signal transmission through a metal wire by an electric signal, it is necessary to increase a line diameter of the metal wire or use a plurality of metal wires in order to transmit a necessary signal amount. Therefore, it is likely that an insertion section will be increased in thickness for wiring.

In order to reduce the insertion section in diameter to be less invasive, optical signal transmission through a thin optical fiber by an optical signal instead of the electric signal is preferable. For the optical signal transmission, an optical transducer of an E/O type (an electrooptic converter) that converts an electric signal into an optical signal and an optical transducer of an O/E type (a photoelectric converter) that converts an optical signal into an electric signal are used.

For a reduction in a diameter of an insertion section of an endoscope, a reduction in size of an optical transducer is important.

International Publication No. 2018/037551 discloses an optical transducer including a fiber holding member in which an insertion hole is formed, an optical fiber being inserted into the insertion hole and fixed using resin.

When a distal end face of the optical fiber is not in contact with a bottom surface of the insertion hole, a distance between a light emission region of an optical element and the distal end face of the optical fiber increases. Therefore, transmission efficiency of the optical transducer is deteriorated.

SUMMARY OF THE INVENTION

An optical transducer for endoscope in an embodiment includes: at least one optical element configured to generate an optical signal; at least one optical fiber configured to transmit the optical signal; and a fiber holding member including a first holding member made of a nontransparent material, the first holding member including a first principal surface and a second principal surface on an opposite side of the first principal surface, and a second holding member made of a transparent material, the second holding member including a third principal surface and a fourth principal surface on an opposite side of the third principal surface, the third principal surface being disposed to face the second principal surface, at least one through-hole being formed in the first holding member, the optical fiber being inserted into the first through-hole, the fiber holding member including, on the fourth principal surface, a bonded electrode on which the optical element is mounted, wherein at least one trench connected to the first through-hole and including openings respectively on two parallel side surfaces is formed on the second principal surface of the first holding member, only a part of a distal end portion of the optical fiber inserted into the first through-hole is observable from the openings of the trench, and the optical fiber is fixed to the fiber holding member by transparent resin disposed in the first through-hole and the trench.

An endoscope in another embodiment includes an optical transducer for endoscope, the optical transducer for endoscope including: at least one optical element configured to generate an optical signal; at least one optical fiber configured to transmit the optical signal; and a fiber holding member including a first holding member made of a nontransparent material, the first holding member including a first principal surface and a second principal surface on an opposite side of the first principal surface, and a second holding member made of a transparent material, the second holding member including a third principal surface and a fourth principal surface on an opposite side of the third principal surface, the third principal surface being disposed to face the second principal surface, at least one through-hole being formed in the first holding member, the optical fiber being inserted into the first through-hole, the fiber holding member including, on the fourth principal surface, a bonded electrode on which the optical element is mounted, wherein at least one trench connected to the first through-hole and including openings respectively on two parallel side surfaces is formed on the second principal surface of the first holding member, only a part of a distal end portion of the optical fiber inserted into the first through-hole is observable from the openings of the trench, and the optical fiber is fixed to the fiber holding member by transparent resin disposed in the first through-hole and the trench.

A manufacturing method for an optical transducer for endoscope in another embodiment, is a manufacturing method for an optical transducer for endoscope, the optical transducer for endoscope including: at least one optical element configured to generate an optical signal; at least one optical fiber configured to transmit the optical signal; and a fiber holding member including a first holding member made of a nontransparent material, the first holding member including a first principal surface and a second principal surface on an opposite side of the first principal surface, and a second holding member made of a transparent material, the second holding member including a third principal surface and a fourth principal surface on an opposite side of the third principal surface, the third principal surface being disposed to face the second principal surface, at least one through-hole being formed in the first holding member, the optical fiber being inserted into the first through-hole, the fiber holding member including, on the fourth principal surface, a bonded electrode on which the optical element is mounted, at least one trench connected to the first through-hole and including openings respectively on two parallel side surfaces being formed on the second principal surface of the first holding member, only a part of a distal end portion of the optical fiber inserted into the first through-hole being observable from the openings of the trench, the optical fiber being fixed to the fiber holding member by transparent resin disposed in the first through-hole and the trench, the manufacturing method including: manufacturing the holding member; injecting the transparent resin uncured into at least one of the first through-hole or the trench; inserting the optical fiber into the first through-hole and bringing a distal end face of the optical fiber into contact with the third principal surface; and curing the transparent resin in a state in which the distal end face is in contact with the third principal surface.

DETAILED DESCRIPTION OF THE PREFERRED EMBODIMENTS

<Endoscope>

Figure 1:
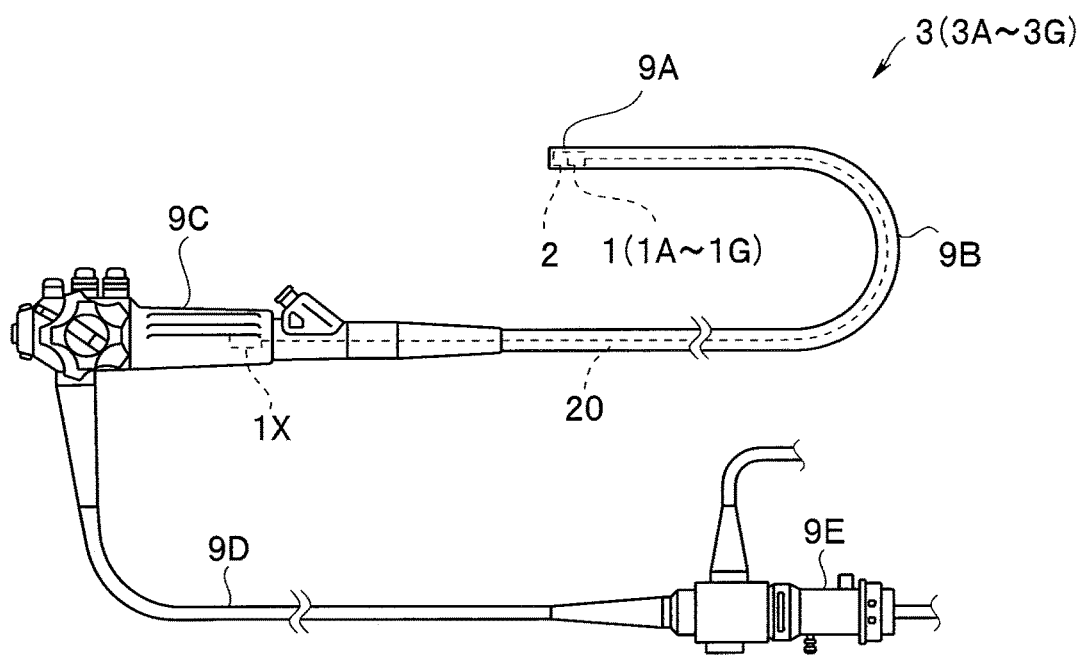
FIG. 1 is a perspective view of an endoscope in an embodiment.

First, an endoscope 3 in an embodiment is explained. As shown in FIG. 1, the endoscope 3 includes an optical transducer 1 (1A to 1G) at a distal end portion 9A of an insertion section 9B.

The endoscope 3 includes the insertion section 9B, at the distal end portion 9A of which an image pickup device 2 with a large number of pixels is disposed, an operation section 9C disposed at a proximal end portion of the insertion section 9B, and a universal cord 9D extending from the operation section 9C.

An electric signal outputted by the image pickup device 2 is converted into an optical signal by the optical transducer 1 (1A to 1G) of an E/O type. The optical signal is transmitted to an optical transducer 1X of an O/E type disposed in the operation section 9C, an optical element of the optical transducer 1X being a photodiode, by being transmitted through an optical fiber 20 inserted through the insertion section 9B. The optical signal is converted into an electric signal by the optical transducer 1X. The processor performs signal processing for causing a display apparatus, for example, a monitor to display an electric signal converted by the optical transducer 1X of the O/E type.

As explained above, the optical transducer 1 (1A to 1G) is small in size and has high reliability and productivity. Accordingly, since the insertion section of the endoscope 3 has a small diameter, the endoscope 3 is less invasive and has high reliability and productivity.

Note that the optical transducer 1X is disposed in the operation section 9C having a relatively large disposition space but may have the same configuration as a configuration of the optical transducer 1 of the present invention. The endoscope 3 is a flexible endoscope but may be a rigid endoscope. A use of the endoscope 3 may be either a medical use or an industrial use. The optical transducer 1X may be disposed in a connector 9E disposed at a proximal end portion of the universal cord 9D.

First Embodiment

Figure 2:
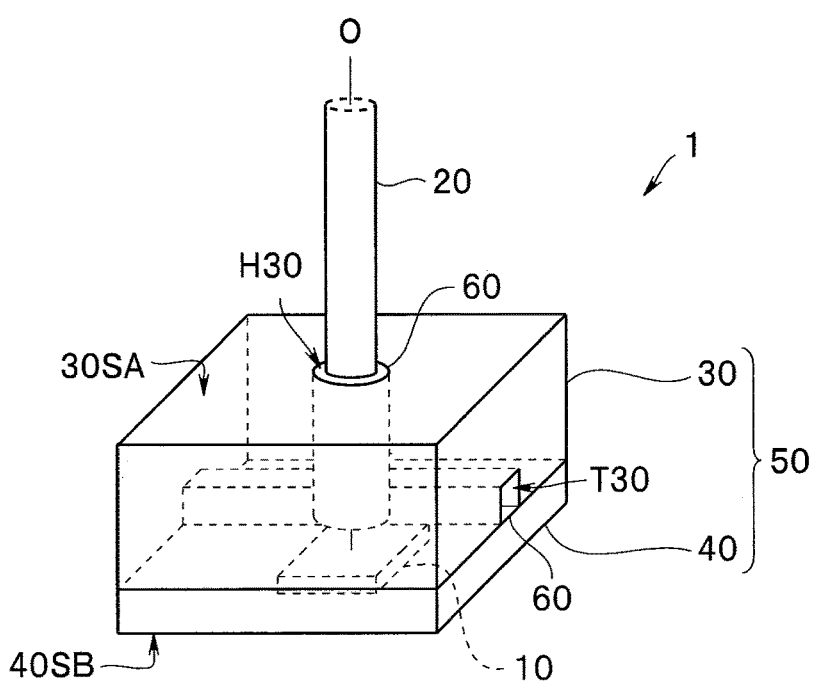
FIG. 2 is a perspective view of an optical transducer in a first embodiment.
Figure 3:
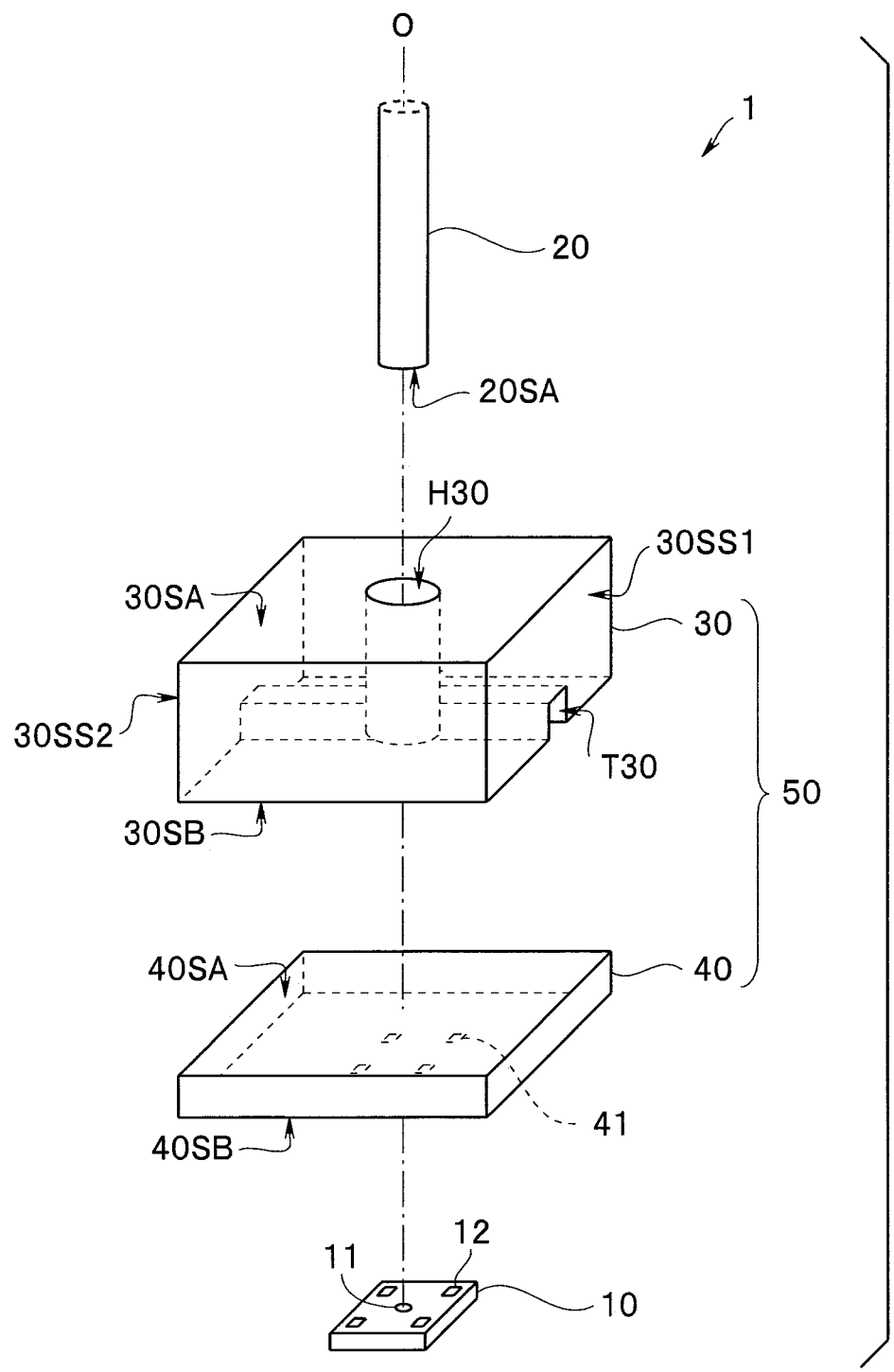
FIG. 3 is a perspective exploded view of the optical transducer in the first embodiment.

An optical transducer for endoscope 1 (hereinafter referred to as an "optical transducer 1") in a first embodiment is explained with reference to FIG. 2 to FIG. 4. In the following explanation, drawings based on respective embodiments are schematic. Relations between thicknesses and widths of respective portions, ratios of the thicknesses of the respective portions, and the like are different from real ones. Portions having different relations and ratios of dimensions of the portions are included among the drawings. A part of components are not illustrated and are not denoted by reference numerals and signs.

The optical transducer 1 is an ultrasmall E/O type module (electrooptic converter) that converts an electric signal outputted by the image pickup device 2 of the endoscope 3 into an optical signal and transmits the optical signal.

The optical transducer 1 includes an optical element 10, an optical fiber 20, and a fiber holding member 50.

The optical element 10 is a light emitting element including a light emission region 11 for outputting an optical signal. The optical element 10 ultrasmall in size having a plan view dimension of 235 µm×235 µm includes, on a light emission surface, the light emission region 11 having a diameter of 10 µm that outputs an optical signal and 70 µm-square four external electrodes 12 connected to the light emission region 11. Note that two of the four external electrodes 12 are dummy electrodes.

The optical fiber 20 for transmitting an optical signal includes, for example, a core having a diameter of 62.5 µm and a clad having a diameter of 80 µm covering an outer circumference of the core. Note that an outer circumference of the clad of the optical fiber 20 may be protected by coating.

The fiber holding member 50, which is a ferrule, includes a first holding member (a perforated plate) 30 made of a nontransparent material and a second holding member (a transparent plate) 40, which is a flat plate made of a transparent material. For example, the first holding member 30 is made of silicon and the second holding member 40 is made of a glass plate.

The first holding member 30 includes a first principal surface 30SA and a second principal surface 30SB on an opposite side of the first principal surface 30SA. The second holding member 40 includes a third principal surface 40SA and a fourth principal surface 40SB on an opposite side of the third principal surface 40SA. The second principal surface 30SB of the first holding member 30 and the third principal surface 40SA of the second holding member 40 are bonded.

In the fiber holding member 50, for example, the first principal surface 30SA is ultrasmall with a lateral width of 1 mm and a longitudinal width of 0.5 mm. The first holding member 30 has a thickness of 500 μm and the second holding member 40 has a thickness of 25 μm.

Bonded electrodes 41 are disposed on the fourth principal surface 40SB, that is, in the second holding member 40 of the fiber holding member 50. The external electrodes 12 of the optical element 10 are bonded to the bonded electrodes 41. The bonded electrodes 41 are connected to a not-shown wire for transmitting a driving signal based on a signal outputted by the image pickup device 2.

In the first holding member 30, a first through-hole H30 piercing through the first principal surface 30SA and the second principal surface 30SB is formed. Since the first through-hole H30 pierces through the first holding member 30, a wall surface of the first through-hole H30 is made of silicon. The first through-hole H30 is bottomed and a bottom surface of the first through-hole H30 is the third principal surface 40SA of the second holding member 40. The optical fiber 20 is inserted into the first through-hole H30. An inner diameter of the first through-hole H30 is, for example, 85 μm, which is slightly larger than an outer diameter of the optical fiber 20. Therefore, an outer circumferential surface of the optical fiber 20 can be regarded as being in contact with the wall surface of the first through-hole H30. Note that when the optical fiber 20 includes the coating covering the clad and an outer diameter of the coating is, for example, 95 μm, the inner diameter of the first through-hole H30 is 100 μm.

The first through-hole H30 is present in a position facing the light emission region 11 of the optical element 10. Therefore, a center axis of the optical fiber 20 inserted into the first through-hole H30 coincides with an optical axis O of the optical element 10. In other words, the optical fiber 20 is optically combined with the optical element 10.

On the second principal surface 30SB of the first holding member 30, a trench T30 connected to the first through-hole H30 and having openings respectively in two parallel side surfaces 30SS1 and 30SS2 is formed. A width of the trench T30 is, for example, 50 μm, which is smaller than the inner diameter of the first through-hole H30. A center axis of a major axis of the first through-hole H30 overlaps a substantial center of the linear trench T30. In other words, in a portion where the trench T30 and the first through-hole H30 are connected, a recess, which is a surface common to a part of a side surface of the first through-hole H30, is present in each of side surfaces on both sides of the trench T30.

Figure 4:
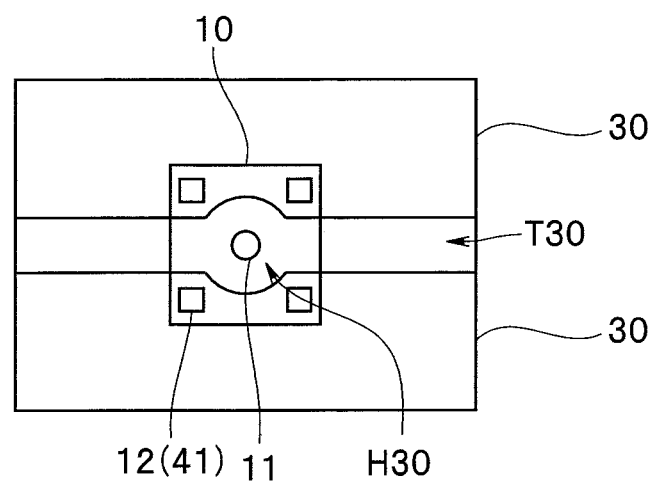
FIG. 4 is a top transparent view of the optical transducer in the first embodiment.

Note that, as shown in FIG. 4, the trench T30 is not formed in regions of the second principal surface 30SB facing the bonded electrodes 41 bonded to the external electrodes 12 of the optical element 10. This is to prevent the thin second holding member 40 from being broken when the external electrodes 12 of the optical element 10 are bonded to the bonded electrode.

The optical fiber 20 is fixed to the fiber holding member 50 by transparent resin 60 disposed in the first through-hole H30 and the trench T30.

It is possible to observe from the openings of the trench T30 that, in the optical transducer 1, a part of a distal end face 20SA of the optical fiber 20 inserted into the first through-hole H30 is in contact with the third principal surface 40SA.

Since the width of the trench T30 is smaller than the inner diameter of the first through-hole H30, only a part of a distal end portion of the optical fiber 20 can be observed from the openings of the trench T30. The entire distal end portion of the optical fiber 20 can be observed if the width of the trench T30 is increased or the fiber holding member is configured by a transparent member. However, when the width of the trench is increased, positioning accuracy in an in-plane direction (an optical axis orthogonal direction) of the optical fiber 20 is deteriorated. When the fiber holding member is configured by the transparent material, it is not easy to accurately form the first through-hole H30.

The width of the trench T30 is preferably larger than 10% and smaller than 50% of an outer diameter of the distal end portion of the optical fiber 20. If the width of the trench T30 is larger than 10% of the outer diameter, a part of the distal end face 20SA can be observed from the openings of the trench T30. If the width of the trench T30 is smaller than 50% of the outer diameter, the positioning accuracy of the distal end portion of the optical fiber 20 is not deteriorated.

The optical transducer 1 has high transmission efficiency because the distal end face 20SA and the third principal surface 40SA are in contact. Note that, in this specification, "in contact" also includes a state in which a slight gap, for example, a gap equal to or smaller than 5 μm is present between the distal end face 20SA and the third principal surface 40SA and the transparent resin 60 is filled in the gap. The transmission efficiency is not greatly deteriorated even if such a gap filled with the transparent resin 60 is present. The endoscope 3 including the ultrasmall optical transducer 1 is less invasive and is capable of performing high-speed transmission of a high-definition video signal.

<Manufacturing Method for the Optical Transducer>

Figure 5:
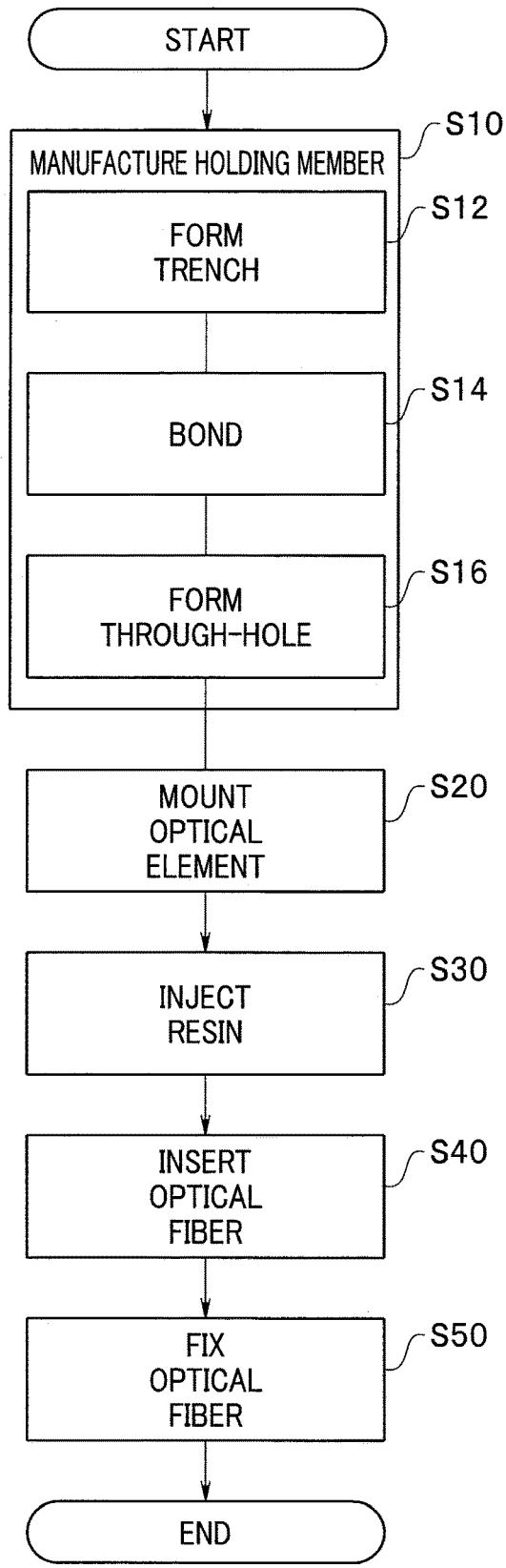
FIG. 5 is a flowchart of a manufacturing method for the optical transducer in the first embodiment.

A manufacturing method for the optical transducer 1 is explained with reference to a flowchart of FIG. 5.

<Step S10> Holding Member Manufacturing Step

A holding member manufacturing step S10 includes a trench forming step (step S12), a bonding step (step S14), and a through-hole forming step (step S16).

A holding member is manufactured by a wafer process. In other words, the first through-hole H30 is formed in a bonded wafer obtained by bonding a glass wafer and a silicon wafer in which a trench T20 is formed. Then, the bonded wafer is singulated by cutting, whereby a plurality of fiber holding members 50, each of which includes the first holding member 30 and the second holding member 40, are manufactured.

Note that an external shape of the fiber holding member 50 is a rectangular parallelepiped shape but may be a columnar shape or a polygonal prism shape.

<Step S12> Trench Forming Step

To form the trench T20 in the silicon wafer, for example, machining using a dicing blade or etching is performed.

<Step S14> Bonding Step

A surface of the silicon wafer on which the trench T20 is formed and the glass wafer are, for example, anodically bonded. The silicon wafer and the glass wafer may be bonded using a transparent adhesive.

<Step S16> Through-Hole Forming Step

The first through-hole H30 is formed by etching of the bonded wafer. The first through-hole H30, a wall surface of which is substantially perpendicular to a principal surface thereof, can be accurately and easily formed by, for example, a reactive ion etching (RIE) method. In the RIE method, the glass wafer functions as an etching stop layer. Therefore, the first through-hole H30 including the third principal surface 40SA of the second holding member 40 as a bottom surface is formed.

The first through-hole H30 may be formed by wet etching. A shape of the first through-hole H30 may be, besides a columnar shape, a prism shape if the optical fiber 20 can be held. The shape of the first through-hole H30 may be a taper shape, a diameter of an opening of which is larger than a diameter of a bottom surface thereof.

Note that transmission efficiency is deteriorated when the second holding member 40 is thick. A thin glass wafer is not easily handled. Accordingly, it is preferable to bond a glass wafer having less easily broken thickness to the silicon wafer and then machine the glass wafer into a thin layer having a thickness larger than 5 μm and smaller than 50 μm.

In other words, if the thickness of the second holding member 40 is smaller than 50 μm, the transmission efficiency is high because 95% or more of light having a wavelength of an optical signal is transmitted. Note that the second holding member 40 is less easily broken in later processes if the thickness is larger than 5 μm.

Note that a thickness of the first holding member 30 is preferably larger than 100 μm in order to stably hold the optical fiber 20.

The bonded electrodes 41 and the like are disposed on the fourth principal surface 40SB of the bonded wafer. A plurality of fiber holding members 50 are manufactured by cutting the bonded wafer.

<Step S20> Optical Element Mounting Step

The optical element 10 is mounted on the fourth principal surface 40SB of the fiber holding member 50. When the external electrodes 12 of the optical element 10 are, for example, ultrasonically bonded to the bonded electrodes 41, the light emission region 11 of the optical element 10 is fixed in a position facing the first through-hole H30. Note that the bonded wafer on which a plurality of optical elements 10 are mounted may be cut. Side-fill resin or under-fill resin for transmitting the light having the wavelength of the optical element may be disposed in bonded sections of the external electrodes 12 of the optical element 10 and the bonded electrodes 41.

When the optical element 10 is bonded, stress is applied to the fourth principal surface 40SB of the fiber holding member 50. However, as explained above, in the fiber holding member 50, the trench T30 is not formed in opposed regions facing regions where the bonded electrodes 41 are disposed in the fourth principal surface 40SB, that is, regions where the external electrodes 12 are bonded in the optical element 10. The regions where the bonded electrodes 41 are disposed in the fourth principal surface 40SB are reinforced because the first holding member 30 is present. Accordingly, it is unlikely that the thin second holding member 40 will be broken when the optical element 10 is bonded. The optical transducer 1 has high reliability because bonding pressure can be set high, for example, when the optical element 10 is ultrasonically bonded.

<Step S30> Resin Injecting Step

The transparent resin 60 in a liquid state before curing is injected from the first through-hole H30 of the fiber holding member 50. As the transparent resin 60, ultraviolet-curable resin or uv- and thermo-curable resin, for example, silicone resin or epoxy resin having high light transmittance is used.

<Step S40> Optical Fiber Inserting Step

Figure 6:
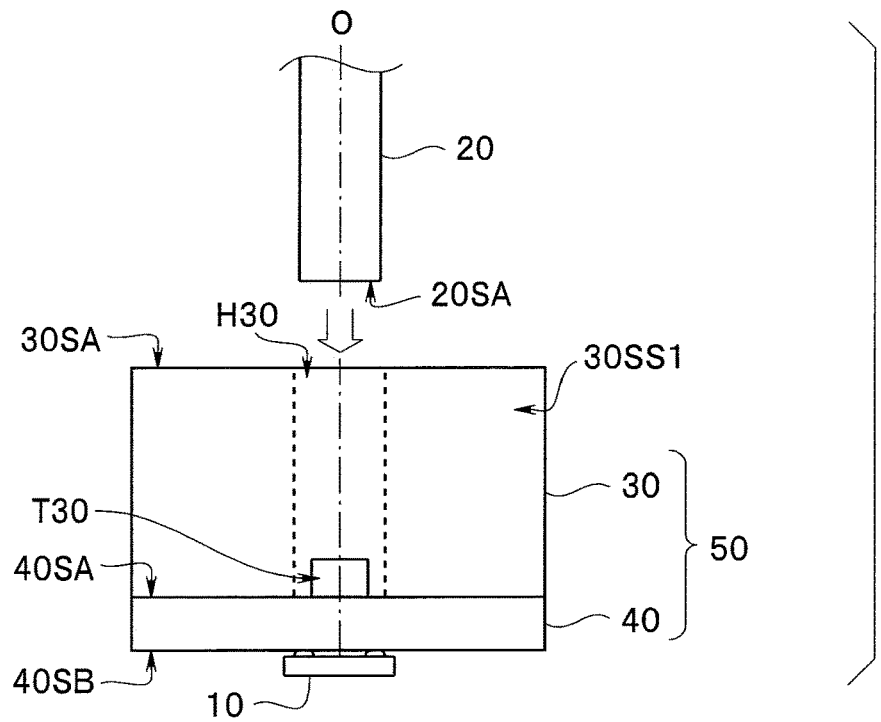
FIG. 6 is a side view for explaining the manufacturing method for the optical transducer in the first embodiment.
Figure 7:
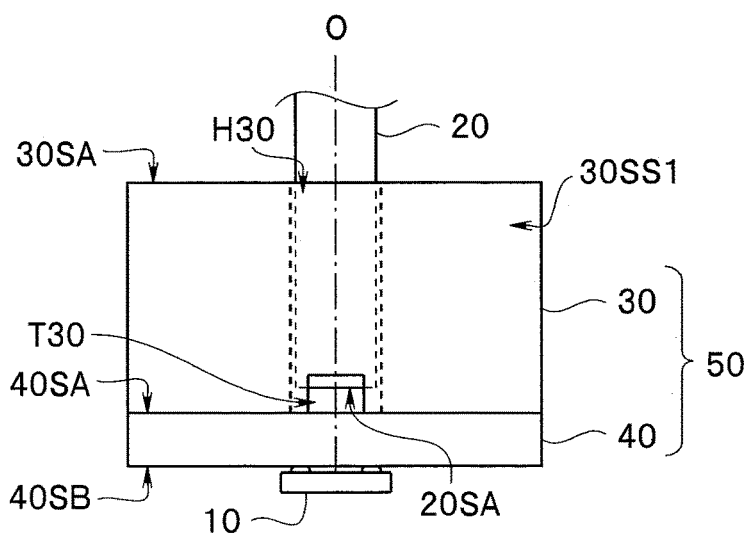
FIG. 7 is a side view for explaining the manufacturing method for the optical transducer in the first embodiment.
Figure 8:
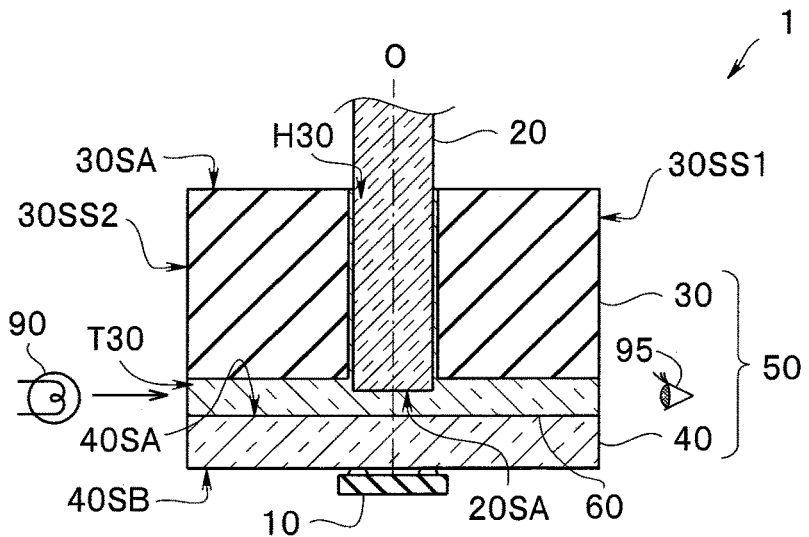
FIG. 8 is a sectional view for explaining the manufacturing method for the optical transducer in the first embodiment.
Figure 9:
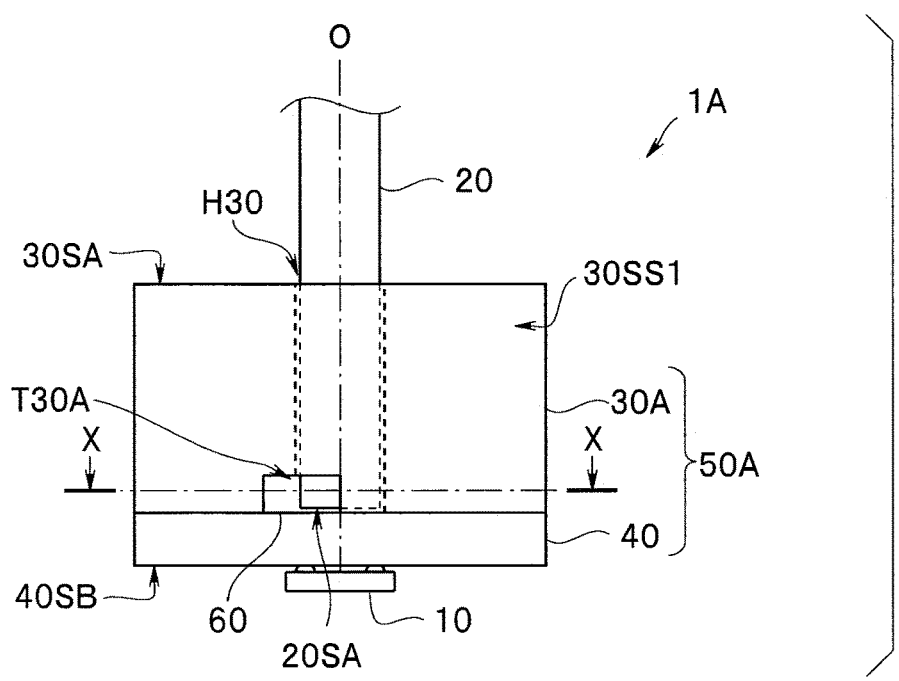
FIG. 9 is a side view of an optical transducer in a modification 1 of the first embodiment.

As shown in FIG. 6, FIG. 7, and FIG. 8, the optical fiber 20 is inserted into the first through-hole H30 and the distal end face 20SA of the optical fiber 20 comes into contact with the third principal surface 40SA.

Note that when the optical fiber 20 is inserted into the first through-hole H30 into which the uncured transparent resin 60 is injected, it is likely that pressure will be applied to the second holding member 40 by the transparent resin 60 pushed by the optical fiber 20 and the second holding member 40 will be broken. In the fiber holding member 50, the transparent resin 60 pushed by the optical fiber 20 flows into the trench T20. Therefore, it is unlikely that the second holding member 40 will be damaged.

Note that, after the optical fiber 20 is inserted into the first through-hole H30, the transparent resin 60 may be injected into the first through-hole H30 by being injected through the trench T30. In other words, in the injecting step S30, the transparent resin 60 may be injected into at least one of the first through-hole H30 or the trench T30. The injecting step S30 may be performed after the inserting step S40.

As shown in FIG. 7 and FIG. 8, in the inserting step S40, it can be confirmed from the openings of the trench T20 that the distal end face 20SA of the optical fiber 20 is in a contact state with the third principal surface 40SA. The confirmation may be directly performed by an eye 95 of an operator or may be performed using a microscope or using a video monitor.

In particular, by irradiating, as shown in FIG. 8, using a light source 90, illumination light having a wavelength at which the transparent resin 60 is not cured, that is, a wavelength longer than a wavelength of ultraviolet light, from one opening of the trench T30, it is easy to confirm the contact of the distal end face 20SA and the third principal surface 40SA from the other opening.

<Step S50> Optical Fiber Fixing Step

The optical fiber 20 is fixed to the fiber holding member 50 by curing the transparent resin 60 in a state in which the distal end face 20SA of the optical fiber 20 is in contact with the third principal surface 40SA.

Ultraviolet light for curing the transparent resin 60 is made incident from at least any one of the openings of the trench T30. For example, observation is performed in a state in which an ultraviolet-ray cut filter is disposed in an optical path of the light source 90 that generates light including visible light and ultraviolet light. Curing is performed by detaching the ultraviolet-ray cut filter from the optical path.

In the ultrasmall optical transducer 1, work for fixing the optical fiber 20 to the fiber holding member (ferrule) 50 is not easy. It is likely that the optical fiber 20 will move after being inserted into the first through-hole H30 and before being fixed. It is not easy to irradiate, with an ultraviolet ray for curing, the transparent resin 60 disposed in a gap between the optical fiber 20 and the first through-hole H30. If the curing of the transparent resin 60 is insufficient, it is likely that the fixing of the optical fiber 20 will be insufficient and the reliability of the optical transducer 1 will be deteriorated.

In a state in which the contact of the distal end face 20SA with the third principal surface 40SA is confirmed from the openings of the trench T30, an ultraviolet ray is immediately made incident from the openings of the trench T30. The optical fiber 20 is fixed by the transparent resin disposed in the trench T30. Naturally, thereafter, the transparent resin 60 disposed in the gap between the optical fiber 20 and the first through-hole H30 is preferably also irradiated with the ultraviolet ray.

As explained above, the manufacturing method for the optical transducer in the present embodiment is easy. It is possible to manufacture an optical transducer having high transmission efficiency.

<Modifications of the First Embodiment>

Optical transducers 1A to 1E in modifications of the first embodiment are similar to the optical transducer 1 and have the same effects as the effects of the optical transducer 1. Therefore, components having the same functions are denoted by the same reference numerals and signs and explanation of the components is omitted.

<Modification 1 of the First Embodiment>

Figure 10:
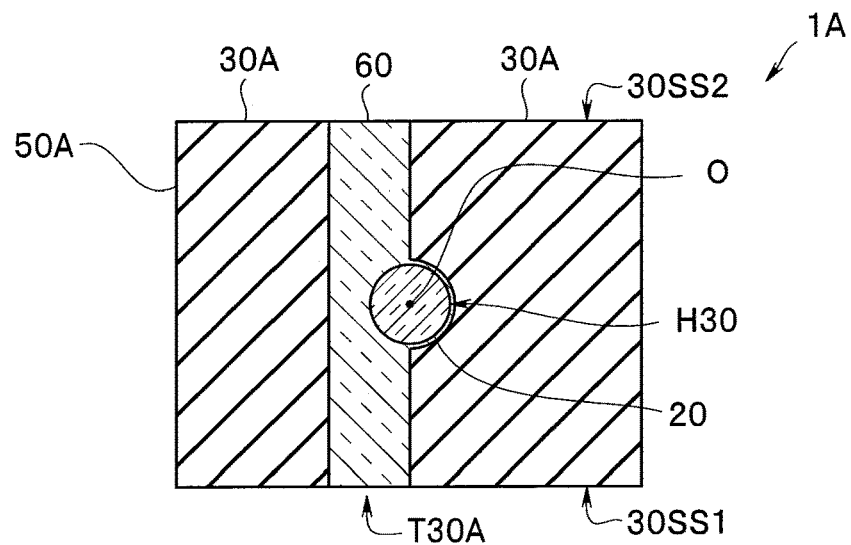
FIG. 10 is a sectional view taken along a X-X line in FIG. 9.

In the optical transducer 1, the center axis in the longitudinal direction of the trench T30 crosses the center axis (optical axis O) of the first through-hole H30. In contrast, as shown in FIG. 10, in the optical transducer 1A in a modification 1, a center axis of a trench T30A of a holding member 50A (first holding member 30A) does not cross the center axis (optical axis O) of the first through-hole H30. In other words, in a portion where the trench T30 and the first through-hole H30 are connected, a recess, which is a surface common to a part of the side surface of the first through-hole H30, is present on a side surface on one side of the trench T30A.

The trench T30A can be set to a width larger than the inner diameter of the first through-hole H30. Accordingly, it is easy to observe the optical transducer 1A from the openings.

In other words, if the contact of the distal end face 20SA with the third principal surface 40SA can be confirmed from the openings of the trench, a positional relation between the trench and the first through-hole is not limited to the configuration of the optical transducer 1. Note that, in order to stably hold the optical fiber 20 and enable a part of the distal end portion to be observed, the optical fiber 20 is preferably in contact with a wall surface of the recess of the trench T30A at more than 180 degrees and less than 300 degrees of the outer circumferential surface of the circular distal end portion. In other words, the center axis (optical axis O) of the first through-hole H30 is preferably located further on an outer side than a wall surface of the trench T30A.

<Modification 2 of the First Embodiment>

Figure 11:
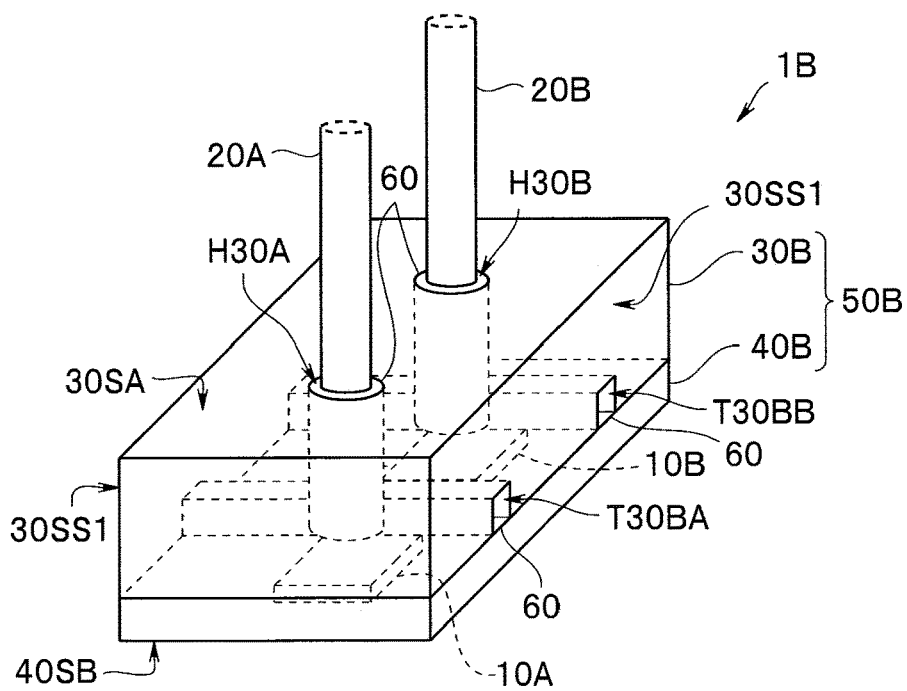
FIG. 11 is a perspective view of an optical transducer in a modification 2 of the first embodiment.
Figure 12:
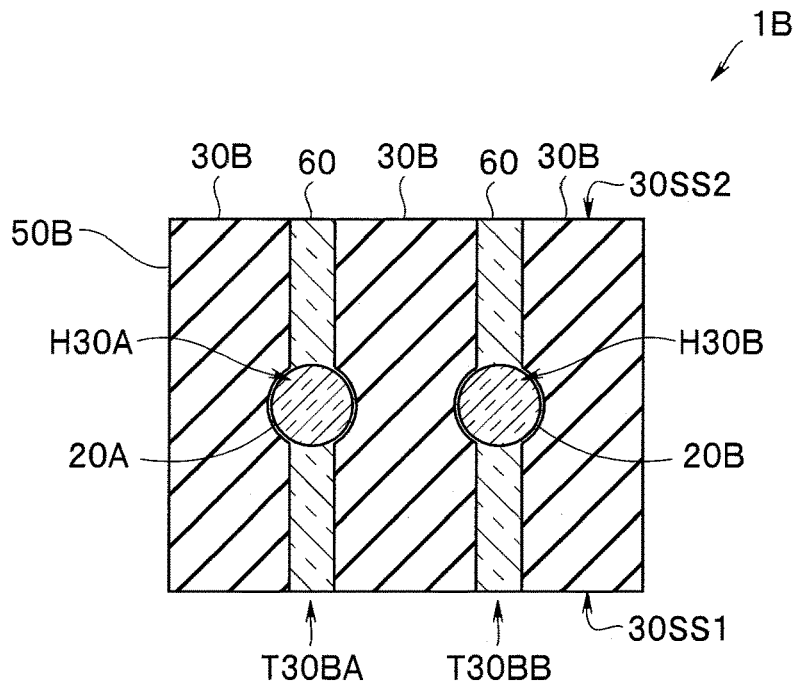
FIG. 12 is a sectional view of the optical transducer in the modification 2 of the first embodiment.

The optical transducer 1B shown in FIG. 11 and FIG. 12 includes two optical elements 10A and 10B, two optical fibers 20A and 20B, and a fiber holding member 50B in which two first through-holes H30A and H30B and two trenches T30BA and T30BB are formed.

The fiber holding member 50B (first holding member 30B) includes a first holding member 30B made of silicon and a second holding member 40B made of glass in which the two first through-holes H30A and H30B and the two trenches T30BA and T30BB are formed.

For example, an optical signal generated by the optical element 10A is transmitted by being transmitted through the optical fiber 20A inserted into the first through-hole H30A. A position of a distal end face of the optical fiber 20A can be confirmed from openings of the trenches T30BA.

Note that, it goes without saying that the optical transducer of the present invention may include three or more optical elements, three or more optical fibers, and a fiber holding member in which three or more first through-holes and three or more trenches are formed.

<Modification 3 of the First Embodiment>

Figure 13:
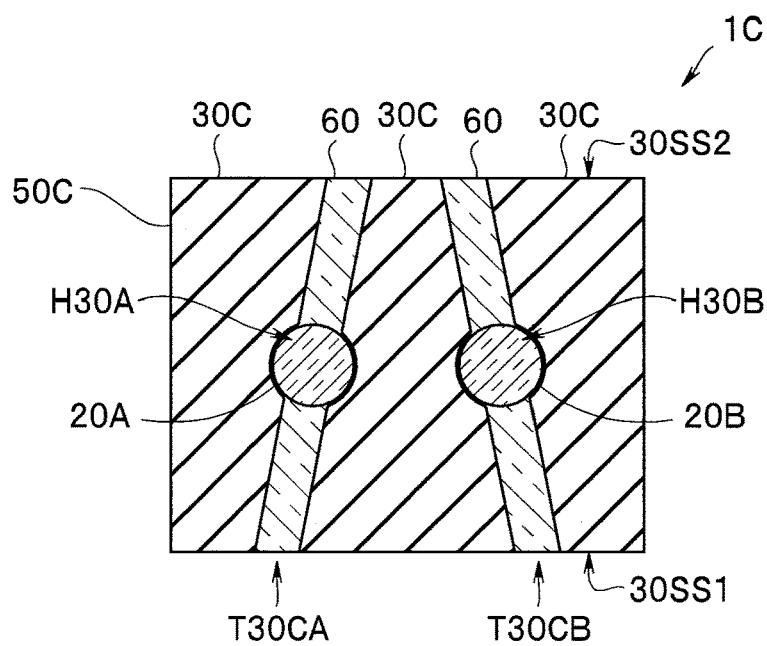
FIG. 13 is a sectional view of an optical transducer in a modification 3 of the first embodiment.

In the optical transducer 1C shown in FIG. 13, a trench T30CA is not parallel to a trench T30CB in an optical fiber holding member 50C (first holding member 30C).

As explained above, the trench T30 is preferably formed to avoid the regions facing the bonded electrodes 41 bonded to the external electrodes 12. In the optical transducer 1C, although not shown, a disposition state of the external electrodes 12 of the optical element is different from the disposition state in the optical transducer 1. Since the two trenches T30CA and T30CB are formed to avoid the regions facing the bonded electrodes 41, the trench T30CA is not parallel to the trench T30CB.

Respective openings on one end of the two trenches T30CA and T30CB are close to each other. Therefore, illumination light and ultraviolet light can be simultaneously made incident on the two trenches T30CA and T30CB from one light source disposed on the side surface 30SS2 side. The other openings of the two trenches T30CA and T30CB on the side surface 30SS1 side are separated from each other. Therefore, when the observation is performed from one of the openings, the observation is less easily affected by illumination light made incident on the other openings. Therefore, the observation is easy.

<Modification 4 of the First Embodiment>

Figure 14:
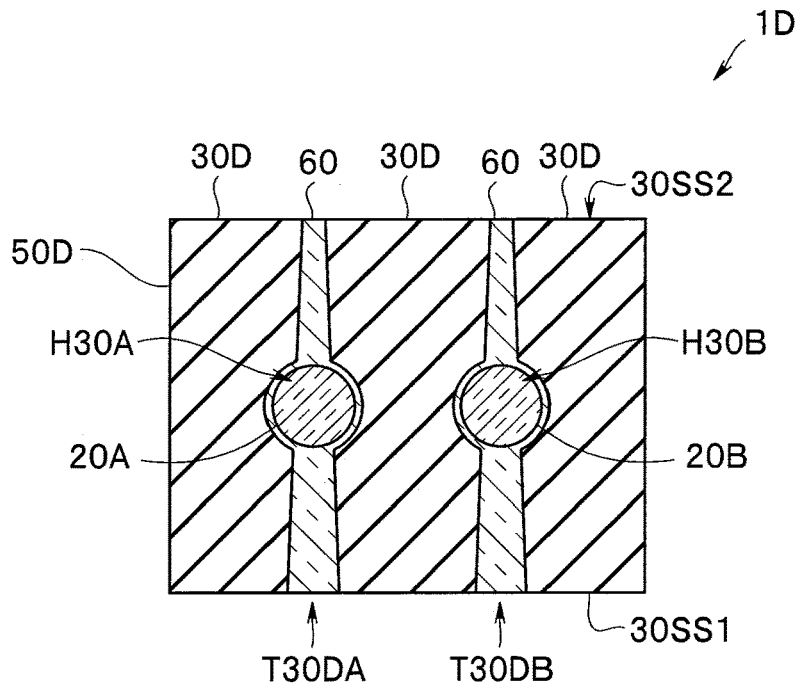
FIG. 14 is a sectional view of an optical transducer in a modification 4 of the first embodiment.

In the optical transducer 1D shown in FIG. 14, two trenches T30DA and T30DB of a fiber holding member 50D (first holding member 30D) have a taper shape, breadth of width of which changes. In the optical transducer 1D, since one of opposed two openings is wide, for example, the observation is easily. It goes without saying that both of the opposed two openings may have the taper shape.

<Modification 5 of the First Embodiment>

Figure 15:
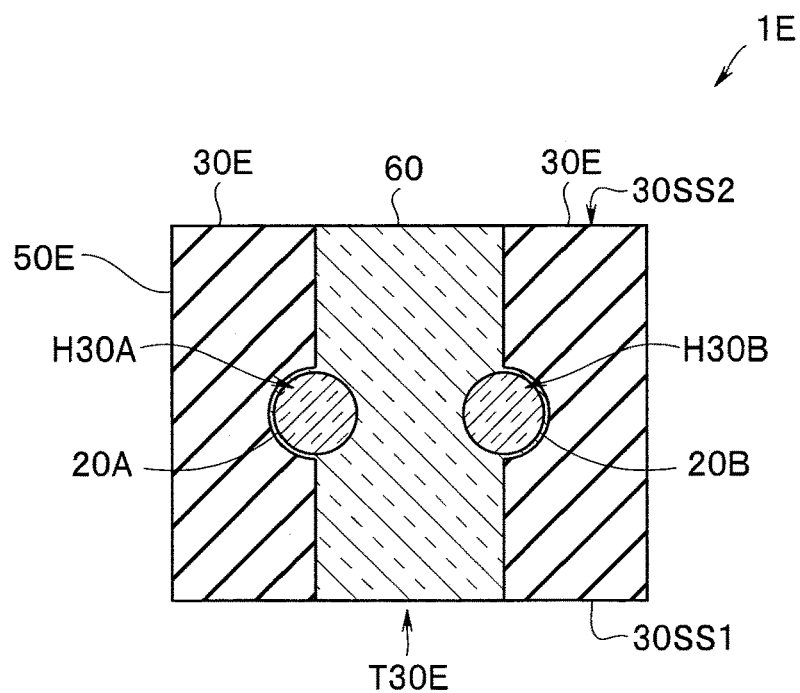
FIG. 15 is a sectional view of an optical transducer in a modification 5 of the first embodiment.

In the optical transducer 1E shown in FIG. 15, one trench T30E of a fiber holding member 50E (first holding member 30E) is connected to the two first through-holes H30A and H30B. Note that the optical fibers 20A and 20B are preferably in contact with wall surfaces of respective recesses of the trench T30E at more than 180 degrees and less than 300 degrees of outer circumferential surface of circular distal end portions.

It is easy to manufacture the optical transducer 1E because only one trench T30E is formed. The observation is easy because the trench T30E has a large opening on a side surface.

Second Embodiment

An optical transducer 1F in a second embodiment is similar to the optical transducer 1 and has the same effects as the effects of the optical transducer 1. Therefore, components having the same functions are denoted by the same reference numerals and signs and explanation of the components is omitted.

Figure 16:
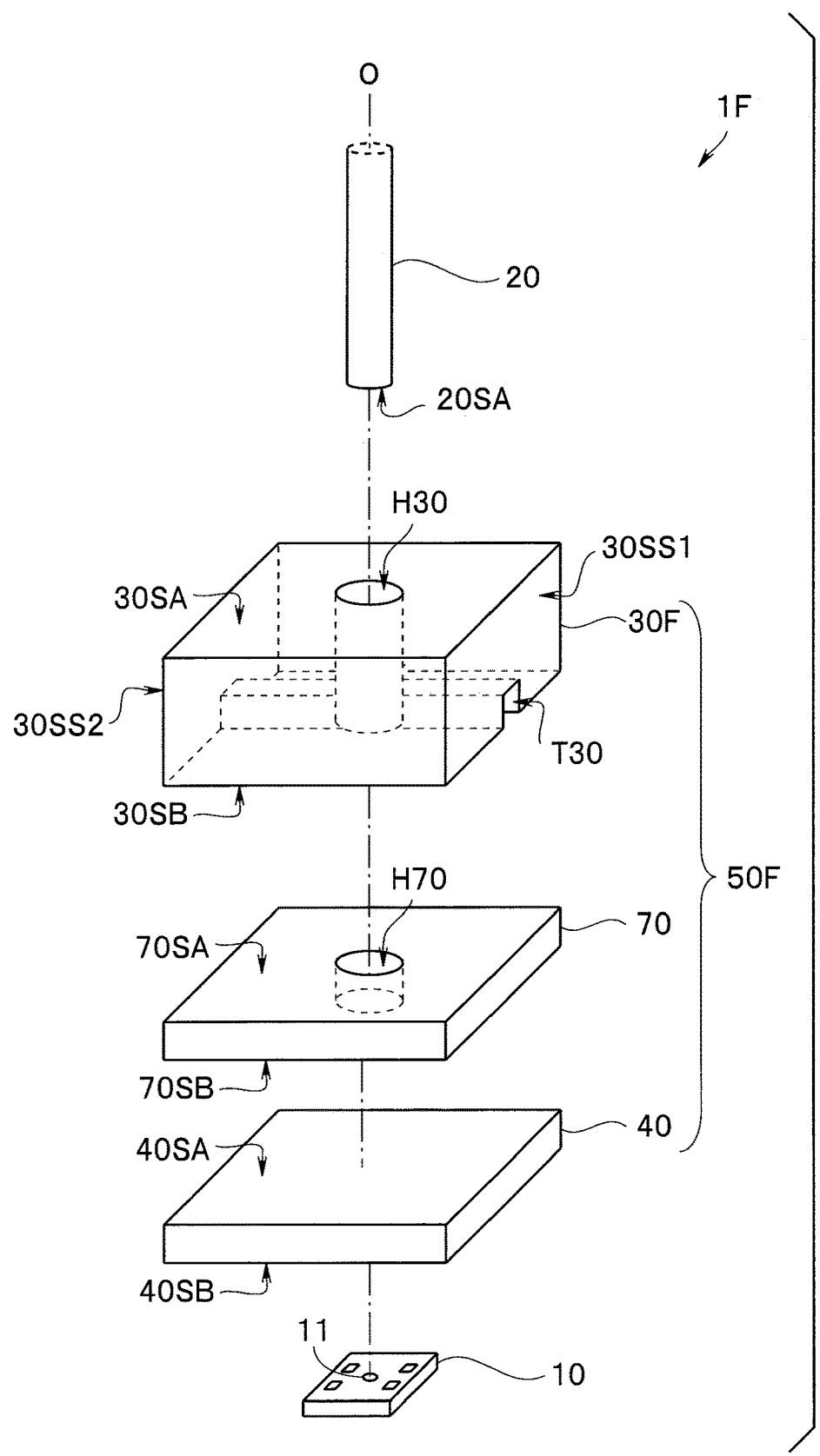
FIG. 16 is a perspective exploded view of an optical transducer in a second embodiment.

A fiber holding member 50F of the optical transducer 1F shown in FIG. 16 further includes a third holding member 70 made of a nontransparent material.

For example, the third holding member 70 made of silicon includes a fifth principal surface 70SA bonded to the second principal surface 30SB of the first holding member 30 and a sixth principal surface 70SB bonded to the third principal surface 40SA of the second holding member 40.

In the third holding member 70, a second through-hole H70 having the same center as the center of the first through-hole H30 is formed.

In the optical transducer 1F, it cannot be directly confirmed from the openings of the trench T30 that the distal end face 20SA of the optical fiber 20 is in contact with the third principal surface 40SA. However, it can be confirmed that the distal end portion of the optical fiber 20 is inserted into the second through hole H70. Accordingly, it can be confirmed that a distance between the distal end face 20SA and the third principal surface 40SA is smaller than thickness of the third holding member 70. Note that the thickness of the third holding member 70 is preferably 20 μm or less and more preferably 5 μm or less.

In a manufacturing method for the fiber holding member 50F, the third holding member 70 (third holding member wafer) is bonded to the first holding member 30 (first holding member wafer) in which the trench T30 is formed and layer thinning treatment is performed. Further, the second holding member 40 (second holding member wafer) is bonded to the third holding member 70 and a bonded wafer is manufactured. The first through-hole H30 and the second through-hole H70 are continuously formed.

In the optical transducer 1F, the thin second holding member 40 is less easily broken because the second holding member 40 is reinforced by the third holding member 70.

<Modification of the Second Embodiment>

An optical transducer 1G in a modification of the second embodiment is similar to the optical transducer 1F and has the same effects as the effects of the optical transducer 1F. Therefore, components having the same functions are denoted by the same reference numerals and signs and explanation of the components is omitted.

Figure 17:
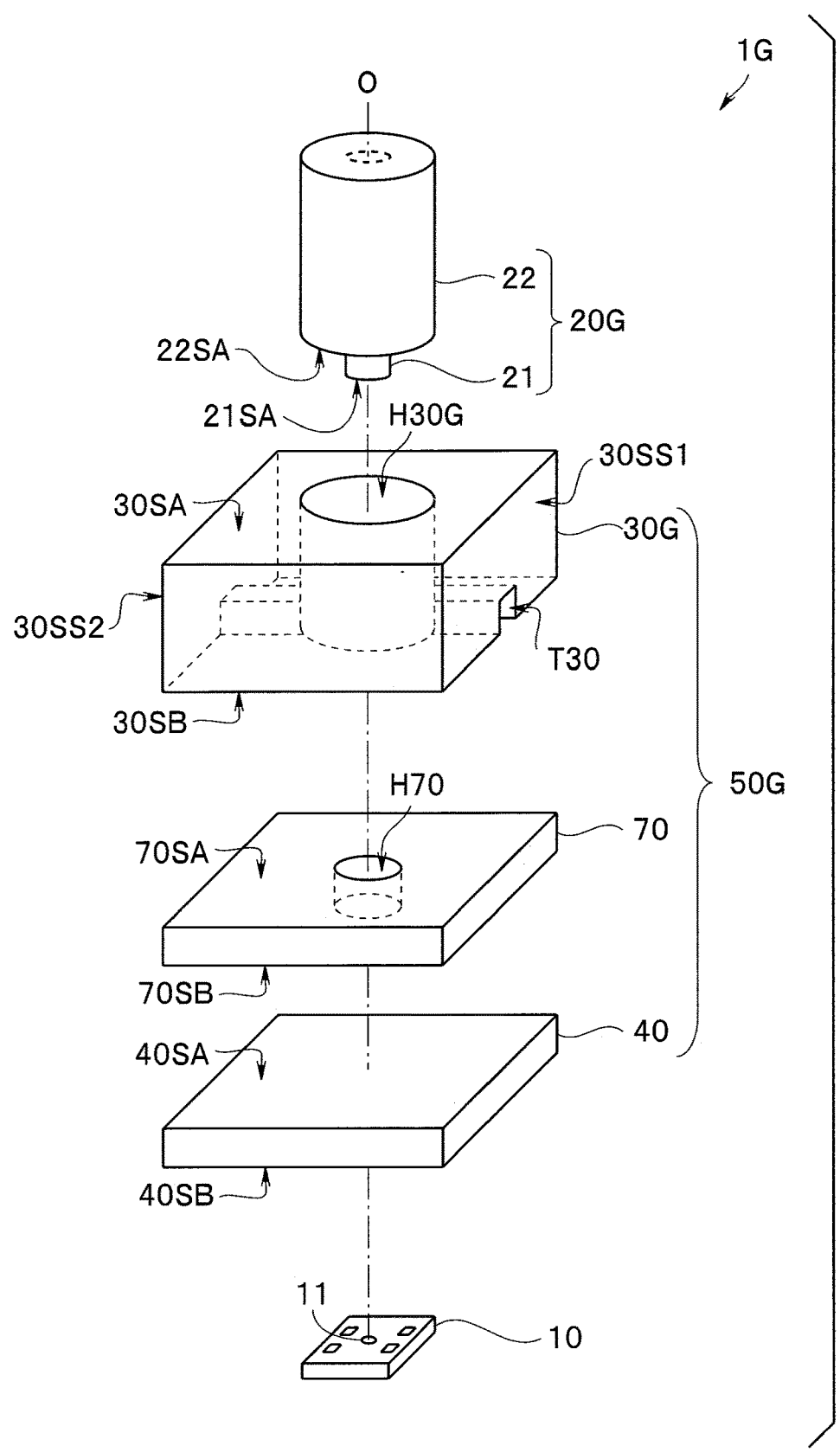
FIG. 17 is a perspective exploded view of an optical transducer in a modification of the second embodiment.

As shown in FIG. 17, in the optical transducer 1G, an optical fiber 20G includes an element wire (glass wire) 21 made of glass for transmitting an optical signal and a coating layer 22 covering the element wire 21. For example, an outer diameter of the coating layer 22 covering a clad having a diameter of 80 μm is 200 μm.

The coating layer 22 covering the element wire 21 including a core and the clad is made of non-halogen resin or polyester elastomer resin. Note that the element wire 21 may include ultraviolet-curable resin covering the clad.

An inner diameter of a first through-hole H30G of a first holding member 30G is, for example, 210 μm, which is slightly larger than the outer diameter of the coating layer 22. On the other hand, an inner diameter of the second through-hole H70 is, for example, 85 μm, which is slightly larger than an inner diameter of the element wire 21.

The element wire 21 covered by the coating layer 22 is inserted into the first through-hole H30G of a fiber holding member 50G. The element wire 21, from which the coating layer 22 is detached, is inserted into the second through-hole H70 of the third holding member 70.

In the optical transducer 1G, it cannot be directly confirmed from the openings of the trench T30 that a distal end face 21SA of the element wire 21 is in contact with the third principal surface 40SA. However, it can be confirmed that a distal end face 22SA of the coating layer 22 is in contact with the fifth principal surface 70SA of the third holding member 70. Accordingly, it can be confirmed that the distance between the distal end face 20SA and the third principal surface 40SA is smaller than the thickness of the third holding member 70.

Note that a length of a region where the element wire 21 of the optical fiber 20G is exposed is preferably substantially the same as the thickness of the third holding member 70. This is because, if the distal end face 22SA of the coating layer 22 is in contact with the fifth principal surface 70SA of the third holding member 70, the distal end face 21SA is in contact with the third principal surface 40SA.

The coating layer 22 has higher visibility than the element wire 21. On the other hand, since only the element wire 21 is inserted into the second through-hole H70, an outer diameter tolerance is small and positioning accuracy of a plane perpendicular to a longitudinal length of an optical fiber is high.

Note that, like the optical transducer 1 and the like, the optical transducer 1F and the optical transducer 10 include only one optical element 10 and one optical fiber 20 (20G).

However, the optical transducer 1F and the optical transducer 1G may include a plurality of optical fibers, a first holding member in which a plurality of first through-holes are formed, and a third holding member in which a plurality of second through-holes are formed.

In the optical transducer 1F and the optical transducer 1G, a shape of a trench may be the same as the shape of the trenches in the optical transducers 1A, 1C, 1D, and 1E.

It goes without saying that the endoscopes 3A to 3F including the optical transducers 1A to 1F have the effects of the endoscope 3 and further have the effects of the optical transducers 1A to 1F.

The present invention is not limited to the embodiments and the modifications explained above. Various changes, combinations, and applications are possible within a range not departing from the gist of the invention.

What is claimed is:

1. An optical transducer for endoscope comprising:
   at least one optical element configured to generate an optical signal;
   at least one optical fiber configured to transmit the optical signal; and
   a fiber holding member including a first holding member made of a nontransparent material, the first holding member including a first principal surface and a second principal surface on an opposite side of the first principal surface, and a second holding member made of a transparent material, the second holding member including a third principal surface and a fourth principal surface on an opposite side of the third principal surface, the third principal surface being disposed to face the second principal surface, at least one through-hole being formed in the first holding member, the optical fiber being inserted into the first through-hole, the fiber holding member including, on the fourth principal surface, a bonded electrode on which the optical element is mounted, wherein
   at least one trench connected to the first through-hole and including openings respectively on two parallel side surfaces is formed on the second principal surface of the first holding member,
   only a part of a distal end portion of the optical fiber inserted into the first through-hole is observable from the openings of the trench, and
   the optical fiber is fixed to the fiber holding member by transparent resin disposed in the first through-hole and the trench.

2. The optical transducer for endoscope according to claim 1, wherein the second principal surface and the third principal surface are bonded.

3. The optical transducer for endoscope according to claim 1, wherein the optical transducer for endoscope comprises:
- a plurality of optical elements;
- a plurality of optical fibers; and
- the first holding member in which a plurality of first through-holes are formed.

4. The optical transducer for endoscope according to claim 1, further comprising a third holding member including a fifth principal surface bonded to the second principal surface and a sixth principal surface bonded to the third principal surface, the third holding member being made of a nontransparent material, at least one second through-hole having a same center as a center of the first through-hole being formed in the third holding member.

5. The optical transducer for endoscope according to claim 4, wherein
the optical fiber includes an element wire for transmitting the optical signal and a coating layer covering the element wire,
the element wire covered by the coating layer is inserted into the first through-hole of the first holding member, and
the element wire, from which the coating layer is detached, is inserted into the second through-hole of the third holding member.

6. The optical transducer for endoscope according to claim 4, wherein the optical transducer for endoscope comprises:
- a plurality of optical elements;
- a plurality of optical fibers;
- the first holding member in which a plurality of first through-holes are formed; and
- the third holding member in which a plurality of second through-holes are formed.

7. The optical transducer for endoscope according to claim 1, wherein the trench is not formed in a region facing the bonded electrode in the second principal surface.

8. A manufacturing method for an optical transducer for endoscope, the optical transducer for endoscope including:
at least one optical element configured to generate an optical signal;
at least one optical fiber configured to transmit the optical signal; and
a fiber holding member including a first holding member made of a nontransparent material, the first holding member including a first principal surface and a second principal surface on an opposite side of the first principal surface, and a second holding member made of a transparent material, the second holding member including a third principal surface and a fourth principal surface on an opposite side of the third principal surface, the third principal surface being disposed to face the second principal surface, at least one through-hole being formed in the first holding member, the optical fiber being inserted into the first through-hole, the fiber holding member including, on the fourth principal surface, a bonded electrode on which the optical element is mounted,
at least one trench connected to the first through-hole and including openings respectively on two parallel side surfaces being formed on the second principal surface of the first holding member,
only a part of a distal end portion of the optical fiber inserted into the first through-hole being observable from the openings of the trench,
the optical fiber being fixed to the fiber holding member by transparent resin disposed in the first through-hole and the trench,
the manufacturing method comprising:
manufacturing the holding member;
injecting the transparent resin uncured into at least one of the first through-hole or the trench;
inserting the optical fiber into the first through-hole and bringing a distal end face of the optical fiber into contact with the third principal surface; and
curing the transparent resin in a state in which the distal end face is in contact with the third principal surface.

9. The manufacturing method for the optical transducer for endoscope according to claim 8, wherein, when the optical fiber is inserted, illumination light that does not cure the transparent resin is made incident from one opening of the trench and the contact of the distal end face with the third principal surface is confirmed from another opening.

10. The manufacturing method for the optical transducer for endoscope according to claim 8, wherein, when the optical fiber is fixed, ultraviolet light for curing the transparent resin is made incident from at least one of the openings of the trench.

11. An endoscope comprising an optical transducer for endoscope,
the optical transducer for endoscope including:
at least one optical element configured to generate an optical signal;
at least one optical fiber configured to transmit the optical signal; and
a fiber holding member including a first holding member made of a nontransparent material, the first holding member including a first principal surface and a second principal surface on an opposite side of the first principal surface, and a second holding member made of a transparent material, the second holding member including a third principal surface and a fourth principal surface on an opposite side of the third principal surface, the third principal surface being disposed to face the second principal surface, at least one through-hole being formed in the first holding member, the optical fiber being inserted into the first through-hole, the fiber holding member including, on the fourth principal surface, a bonded electrode on which the optical element is mounted, wherein
at least one trench connected to the first through-hole and including openings respectively on two parallel side surfaces is formed on the second principal surface of the first holding member,
only a part of a distal end portion of the optical fiber inserted into the first through-hole is observable from the openings of the trench, and
the optical fiber is fixed to the fiber holding member by transparent resin disposed in the first through-hole and the trench.

* * * * *